United States Patent
Bratkovski et al.

(10) Patent No.: US 7,391,511 B1
(45) Date of Patent: Jun. 24, 2008

(54) RAMAN SIGNAL-ENHANCING STRUCTURES AND RAMAN SPECTROSCOPY SYSTEMS INCLUDING SUCH STRUCTURES

(75) Inventors: Alexandre M. Bratkovski, Mountain View, CA (US); Shih-Yuan Wang, Palo Alto, CA (US); Zhiyong Li, Redwood City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 11/700,986

(22) Filed: Jan. 31, 2007

(51) Int. Cl.
*G01J 3/44* (2006.01)
*G01N 21/65* (2006.01)

(52) U.S. Cl. ...................................... 356/301
(58) Field of Classification Search ................ 356/301, 356/303, 317, 318, 326; 438/20
See application file for complete search history.

(56) References Cited

U.S. PATENT DOCUMENTS

| | | | |
|---|---|---|---|
| 4,674,878 A | 6/1987 | Vo-Dinh | |
| 5,017,007 A | 5/1991 | Milne et al. | |
| 5,255,067 A | 10/1993 | Carrabba et al. | |
| 5,527,712 A | 6/1996 | Sheehy | |
| 5,609,907 A | 3/1997 | Natan | |
| 5,772,905 A | 6/1998 | Chou | |
| 5,837,552 A | 11/1998 | Cotton et al. | |
| 6,149,868 A | 11/2000 | Natan et al. | |
| 6,165,911 A | 12/2000 | Calveley | |
| 6,365,059 B1 | 4/2002 | Pechenik | |
| 6,406,777 B1 * | 6/2002 | Boss et al. | 428/209 |
| 6,432,740 B1 | 8/2002 | Chen | |
| 6,623,977 B1 | 9/2003 | Farquharson et al. | |
| 6,649,683 B2 | 11/2003 | Bell | |
| 6,743,368 B2 | 6/2004 | Lee | |
| 6,748,865 B2 | 6/2004 | Sakurai et al. | |
| 6,755,984 B2 | 6/2004 | Lee et al. | |
| 6,759,180 B2 | 7/2004 | Lee | |
| 6,829,988 B2 | 12/2004 | George et al. | |
| 6,861,263 B2 | 3/2005 | Natan | |
| 6,897,158 B2 | 5/2005 | Sharma | |
| 6,916,511 B2 | 7/2005 | Lee et al. | |
| 6,923,930 B2 | 8/2005 | Ling et al. | |
| 6,975,891 B2 | 12/2005 | Pawluczyk | |
| 7,080,596 B2 | 7/2006 | Lee et al. | |
| 2004/0137734 A1 | 7/2004 | Chou et al. | |
| 2004/0161332 A1 * | 8/2004 | Rabinowitz et al. | 415/80 |
| 2005/0150404 A1 | 7/2005 | Lee et al. | |

OTHER PUBLICATIONS

Collier, C.P., et al., Reversible Tuning of Silver Quantum Dot Monolayers Through the Metal-Insulator Transition, Science, Sep. 26, 1997, pp. 1978-1981, vol. 277.

(Continued)

*Primary Examiner*—Gregory J. Toetley, Jr.
*Assistant Examiner*—Abdullahi Nur

(57) ABSTRACT

A Raman signal-enhancing structure includes a substrate and a plurality of protrusions located at predetermined positions relative to a surface of the substrate. Each protrusion includes a Raman signal-enhancing material and has cross-sectional dimensions of less than about 50 nanometers. The structure also includes an edge that includes an intersection between two nonparallel surfaces of at least one protrusion. A Raman spectroscopy system includes such a Raman signal-enhancing structure, and Raman spectroscopy may be performed on an analyte using such structures and systems. A method for forming such a Raman signal-enhancing structure includes nanoimprint lithography.

20 Claims, 11 Drawing Sheets

OTHER PUBLICATIONS

Emory, Steven R., et al., Screening and Enrichment of Metal Nanoparticles with Novel Optical Properties, J. Phys. Chem., B, Jan. 15, 1998, pp. 493-496, vol. 102, No. 3.

Kneipp, Katrin, et al., Single Molecule Detection Using Surface-Enhanced Raman Scattering (SERS), Physical Review Letters, Mar. 3, 1997, pp. 1667-1670, vol. 78, No. 9, The American Physical Society.

Nie, Shuming, et al., Probing Single Molecules and Single Nanparticles by Surface-Enhanced Raman Scattering, Science, Feb. 21, 1997, pp. 1102-1106, vol. 275.

Michaels, et al., Surface Enhanced Raman Spectroscopy of Individual Rhodamine 6G Molecules on Large Ag Nanocrystals, J. Am. Chem. Soc., Oct. 14, 1999, pp. 9932-9939, vol. 121.

Tao, Andrea, et al., Langmuir-Blodgett Silver Nanowire Monolayers for Molecular Sensing Using Surface-Enhanced Raman Spectroscopy, NANO Letters, Aug. 2, 2003, pp. 1229-1233, vol. 3, No. 9.

Garcia-Vidal, F.J., et al., Collective Theory for Surface Enhanced Raman Scattering, Physical Review Letters, Aug. 5, 1996, pp. 1163-1166, vol. 77, No. 6.

Wu, W., et al., One-Kilobit Cross-Bar Molecular Memory Circuits at 30-nm Half-Pitch Fabricated by Nanoimprint Lithography, Applied Physics A, Mar. 11, 2005, pp. 1173-1178, vol. 80.

* cited by examiner

RAMAN SIGNAL-ENHANCING STRUCTURES AND RAMAN SPECTROSCOPY SYSTEMS INCLUDING SUCH STRUCTURES

FIELD OF THE INVENTION

The present invention relates to Raman spectroscopy. More particularly, the invention relates to Raman signal-enhancing structures for enhancing the Raman scattered radiation that is scattered by an analyte, Raman spectroscopy systems including such Raman signal-enhancing structures, and methods for performing Raman spectroscopy using such Raman signal-enhancing structures.

BACKGROUND OF THE INVENTION

Raman spectroscopy is a technique for analyzing molecules or materials. In conventional Raman spectroscopy, an analyte (or sample) that is to be analyzed is irradiated with high intensity monochromatic electromagnetic radiation provided by a radiation source, such as a laser. An electromagnetic radiation detector detects radiation that is scattered by the analyte. The characteristics of the scattered radiation provide information relating to the analyte.

Conventional Raman spectroscopy systems typically include an electromagnetic radiation source that is configured to emit incident electromagnetic radiation, an analyte stage on which an analyte may be positioned, and an electromagnetic radiation detector. The radiation detector is configured to detect at least a portion of scattered radiation that is scattered by the analyte. Raman spectroscopy systems also typically include various optical components positioned between the radiation source and the analyte stage, and between the analyte stage and the radiation detector. Such optical components may include lenses, filters, and apertures.

The radiation source may be a commercially available laser. The wavelength or wavelengths of incident electromagnetic radiation that may be emitted by the electromagnetic radiation source typically are within or near the visible region of the electromagnetic radiation spectrum.

The radiation detector receives and detects at least a portion of the scattered radiation that is scattered by an analyte disposed on the analyte stage. The detector may include a device for determining the wavelength of the scattered radiation (for example, a monochromator) and a device for determining the intensity of the scattered radiation (for example, a photomultiplier). Typically, the scattered radiation is scattered in all directions relative to the analyte stage.

Optical components positioned between the radiation source and the analyte stage are used to collimate, filter, or focus the incident radiation before the incident radiation impinges on the analyte stage. Optical components positioned between the analyte stage and the radiation detector are used to collimate, filter, or focus the scattered radiation.

An analyte may be provided on an analyte stage of a Raman spectroscopy system and irradiated with incident radiation emitted by a radiation source to perform Raman spectroscopy using a Raman spectroscopy system. As the incident radiation impinges on the analyte, at least some of the incident radiation will be scattered by the analyte. A majority of the photons of the incident radiation that impinge on the analyte are elastically scattered by the analyte. In other words, the scattered photons have the same energy, and thus the same wavelength, as the incident photons. This elastic scattering of photons is termed "Rayleigh scattering," and radiation consisting of these elastically scattered photons is termed "Rayleigh scattered radiation" or "Rayleigh radiation."

The Rayleigh scattering process can be further described with reference to the simplified Jablonski diagram shown schematically in FIG. 1, which illustrates various energy levels of a hypothetical analyte. In FIG. 1, energy levels of the analyte are represented as horizontal lines. As seen therein, the ground state energy level (the lowest energy level) is shown at the bottom of the diagram, excited vibrational energy states are shown just above the ground state, excited electronic energy states are shown at the top of the diagram, and virtual excited states are shown between the excited electronic states and the excited vibrational states. As seen in FIG. 1, Rayleigh scattering typically involves absorption of a single photon of the incident radiation by the analyte, which causes the analyte to transition from the ground state to a virtual state followed by relaxation to the ground state. As the analyte relaxes to the ground state, the analyte emits a photon of scattered radiation that has energy equal to that of the photon of the incident radiation. In this manner, the photon of the incident radiation is considered to have been elastically scattered.

In addition to the Rayleigh scattering of photons, a very small fraction of the photons of the incident radiation may be inelastically scattered by the analyte. Raman scattered radiation is also emitted from the analyte. Typically, only about 1 in $10^7$ of the photons of the incident radiation is inelastically scattered by the analyte. These inelastically scattered photons have a different wavelength than the photons of the incident radiation. This inelastic scattering of photons is termed "Raman scattering," and radiation consisting of Raman scattered photons is termed "Raman scattered radiation" or "Raman radiation." The photons of the Raman scattered radiation can have wavelengths less than, or more typically, greater than the wavelength of the photons of the incident radiation.

The Raman scattering process can be further described with reference to the simplified Jablonski diagram shown in FIG. 1. When a photon of the incident radiation collides with the analyte, energy can be transferred from the photon to the analyte or from the analyte to the photon. When energy is transferred form the photon of the incident radiation to the analyte, the Raman scattered photon will have a lower energy and a corresponding longer wavelength than the incident photon. These Raman scattered photons having lower energy than the incident photons are collectively referred to in Raman spectroscopy as the "Stokes radiation." As seen in FIG. 1, 1st order Stokes Raman scattering typically involves absorption of a single photon of the incident radiation by the analyte, which causes the analyte to transition from a first energy state (for example, the ground state) to an excited virtual state. The analyte then relaxes to an excited vibrational state of higher energy than the first energy state. As the analyte relaxes to the excited vibrational state, the analyte emits a photon of scattered radiation that has less energy (and a longer wavelength) than the photon of the incident radiation. In this manner, the photon of the incident radiation is considered to have been inelastically scattered.

When energy is transferred from the analyte to a Raman scattered photon, the Raman scattered photon will have a higher energy and a corresponding shorter wavelength than the photon of the incident radiation. These Raman scattered photons, which have higher energy than the incident photons, are collectively referred to in Raman spectroscopy as the "anti-Stokes radiation." As seen in FIG. 1, 1st order anti-Stokes Raman scattering typically involves absorption of a single photon of the incident radiation by the analyte, which causes the analyte to transition from an excited vibrational energy state to an excited virtual state. The analyte then relaxes to a lower energy state (for example, the ground state) than the excited vibrational energy state. As the analyte relaxes to the lower energy state, the analyte emits a photon of scattered radiation that has more energy (and a shorter wavelength) than the photon of the incident radiation. In this manner, the photon of the incident radiation is considered to have been inelastically scattered.

The shift in energy (wavelength, frequency, or wave number) of the Raman scattered photons in relation to the Rayleigh scattered photons is known as the "Raman shift."

Raman scattering primarily involves a one photon excitation-one photon relaxation process. These Raman scattering processes are often referred to as "1st order" Raman scattering processes. However, multiple photon excitation-single photon relaxation processes are also observed and are referred to as "hyper Raman scattering" processes. Two photon excitation-one photon relaxation scattering processes are referred to as "2nd order" hyper Raman scattering processes, three-photon excitation-one photon relaxation processes are referred to as "3rd order" Raman scattering processes, etc. These higher order Raman scattering processes are often referred to as "harmonics."

In 2nd order scattering processes, a molecule of the analyte in an initial energy state absorbs the energy from two photons of the incident radiation causing an energy transition in the analyte to a virtual excited state, followed by relaxation to a final energy state and emission of a single scattered photon. If the final energy state is the same as the initial energy state, the scattering process is referred to as hyper Raleigh scattering. If the final energy state is higher than the initial energy state, the scattering process is referred to as 2nd order Stokes hyper Raman scattering. Finally, if the final energy state is lower than the initial energy state, the scattering process is referred to as 2nd order anti-Stokes hyper Raman scattering. The Stokes and anti-Stokes 2nd order hyper Raman scattering processes are also represented in the Jablonski diagram shown in FIG. 1.

Information may be obtained from hyper Raman scattered radiation that cannot be obtained from 1st order Raman scattered radiation. In particular, vibrational information may be suppressed in Raman scattered radiation due to symmetry issues, thereby resulting in what are often referred to as "silent modes." These silent modes may not be suppressed in the hyper Raman scattered radiation.

When an analyte is irradiated with incident radiation, the scattered radiation may include Raman scattered radiation, which may comprise 1st order Raman scattered radiation (Stokes and anti-Stokes) and higher order hyper Raman scattered radiation (Stokes and anti-Stokes), in addition to Rayleigh scattered radiation. The Raman scattered radiation that is scattered by the analyte (including the hyper Raman scattered radiation) is often referred to as the "Raman signal."

The Raman signal is detected using the radiation detector. The wavelengths and corresponding intensity of the Raman scattered radiation may be determined and used to provide a Raman spectral graph. Analytes generate unique Raman spectral graphs. The unique Raman spectral graph obtained by performing Raman spectroscopy can be used to obtain information relating to the analyte including, but not limited to, the identification of an unknown analyte, or the determination of physical and chemical characteristics of a known analyte.

The number of Raman scattered photons that are scattered by an analyte is extremely small relative to the number of Rayleigh scattered photons, and the number of hyper Raman scattered photons is even smaller than the number of 1st order Raman scattered photons. Typical radiation detectors are capable of detecting the high-intensity Rayleigh scattered radiation in addition to the low-intensity Raman scattered radiation. The detection of the Raman scattered radiation may be difficult due to the high intensity of the Rayleigh scattered radiation. To overcome this difficulty, a radiation filter may be positioned between the analyte stage and the detector to prevent the Rayleigh scattered radiation from being detected by the detector, thus allowing only the Raman scattered radiation to be received by the detector. Commercially available notch filters may be used for such purposes.

After removal of the Rayleigh scattered radiation, the various wavelengths of Raman scattered radiation typically are spatially separated using a diffraction grating. The separated wavelengths of Raman scattered radiation typically are detected or imaged simultaneously using a charge coupled device (CCD) array. Alternatively, the wavelengths of Raman scattered radiation may be detected using a photomultiplier tube (PMT).

Surface-enhanced Raman spectroscopy (SERS) is a technique that allows for enhancement of the intensity of the Raman scattered radiation relative to conventional Raman spectroscopy (i.e., the number of Raman scattered photons that are scattered by an analyte). In SERS, the analyte typically is adsorbed onto or placed adjacent to what is often referred to as a SERS-active structure. SERS-active structures typically include a metal surface or structure. Interactions between the analyte and the metal surface may cause an increase in the intensity of the Raman scattered radiation.

Several types of metallic structures have been employed in SERS techniques to enhance the intensity of Raman scattered radiation that is scattered by an analyte. Some examples of such structures include electrodes in electrolytic cells, metal colloid solutions, and metal substrates such as a roughened metal surface or metal "islands" formed on a substrate. For example, it has been shown that adsorbing analyte molecules onto or near a specially roughened metal surface of gold or silver can enhance the Raman scattering intensity by factors of between $10^3$ and $10^6$.

Raman spectroscopy recently has been performed employing metal nanoparticles, such as nanometer scale needles, particles, and wires, as opposed to a simple roughened metallic surface. This process will be referred to herein as nano-enhanced Raman spectroscopy (NERS). Structures comprising nanoparticles that are used to enhance the intensity of Raman scattered radiation may be referred to as NERS-active structures. The intensity of the Raman scattered radiation that is scattered by an analyte adsorbed on such a NERS-active structure can be increased by factors as high as $10^{16}$.

BRIEF SUMMARY OF THE INVENTION

In one aspect, the present invention includes a Raman signal-enhancing structure that includes a substrate and a plurality of protrusions located at predetermined positions relative to a surface of the substrate. Each protrusion includes a Raman signal-enhancing material and has cross-sectional dimensions of less than about 50 nanometers. The Raman signal-enhancing structure also includes a plurality of edges. Each edge includes an intersection between two nonparallel surfaces of at least one protrusion.

In another aspect, the present invention includes a method of forming a Raman signal-enhancing structure for use in a spectroscopy system. The method includes providing a nanoimprint mold having a plurality of protrusions extending from a surface thereof, applying a layer of deformable material to a surface of a substrate, and pressing the protrusions of the nanoimprint mold into the deformable material to form a plurality of complementary protrusions in the layer of deformable material. The nanoimprint mold is removed from the layer of deformable material, and a Raman signal-enhancing material is applied over the complementary protrusions in the layer of deformable material to form a plurality of protrusions comprising a Raman-signal enhancing material. The substrate and the deformable material are separated from the plurality of protrusions comprising a Raman-signal enhancing material.

In yet another aspect, the present invention includes a method of performing Raman spectroscopy on an analyte. A Raman signal-enhancing structure is provided that includes at least one edge and a structure configured to position an analyte proximate the at least one edge. An analyte is provided proximate the Raman signal-enhancing structure and positioned proximate the edge using the structure configured to position the analyte. The analyte is irradiated with electromagnetic radiation, and Raman scattered radiation that is scattered by the analyte is detected.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The term "analyte" as used herein means any molecule, molecules, material, substance, or matter that is to be analyzed or detected by Raman spectroscopy.

The term "nanoparticle" as used herein means a particle of any shape having cross-sectional dimensions of less than about 100 nanometers. Examples of nanoparticles include, but are not limited to, nanodots (including quantum dots), nanowires, nanolines, nanocolumns, and nanospheres.

The term "Raman signal-enhancing material" as used herein means a material that, when formed into appropriate geometries or configurations, is capable of increasing the number of Raman scattered photons that are scattered by an analyte when the analyte is located proximate to that material, and when the analyte and material are subjected to electromagnetic radiation. Raman signal-enhancing materials include, but are not limited to, silver, gold, and copper. Raman signal-enhancing materials are used to form Raman signal-enhancing structures.

The term "Raman signal-enhancing structure" as used herein means a structure that is capable of increasing the number of Raman scattered photons that are scattered by an analyte when the analyte is located proximate to the structure, and the analyte and structure are subjected to electromagnetic radiation. Raman signal-enhancing structures include SERS-active structures and NERS-active structures.

The illustrations presented herein are not meant to be actual views of any particular Ramen-enhancing structure or Raman spectroscopy system, but are merely idealized representations which are employed to describe the present invention. Additionally, elements common between figures may retain the same numerical designation.

Figure 2:
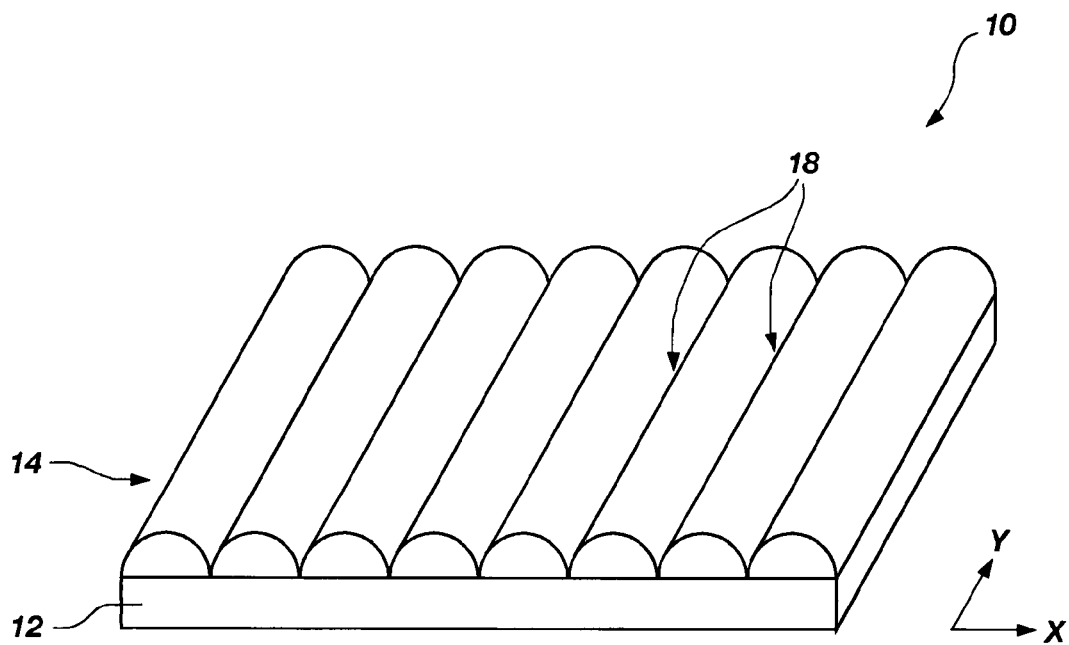
FIG. 2 is a perspective view of a representative Raman signal-enhancing structure that embodies teachings of the present invention.

A representative Raman signal-enhancing structure 10 that embodies teachings of the present invention is shown in FIG. 2. The Raman signal-enhancing structure 10 may include a substrate 12 and a plurality of protrusions 14 on a surface of the substrate 12. The protrusions 14 may be located at predetermined positions on or relative to the surface of the substrate 12. The protrusions 14 may include nanoparticles that are integrally formed with or on the substrate 12. Alternatively, the protrusions 14 may include separate nanoparticles that are merely resting on a surface of the substrate 12. Furthermore, the protrusions 14 may be substantially elongated.

Figure 3:
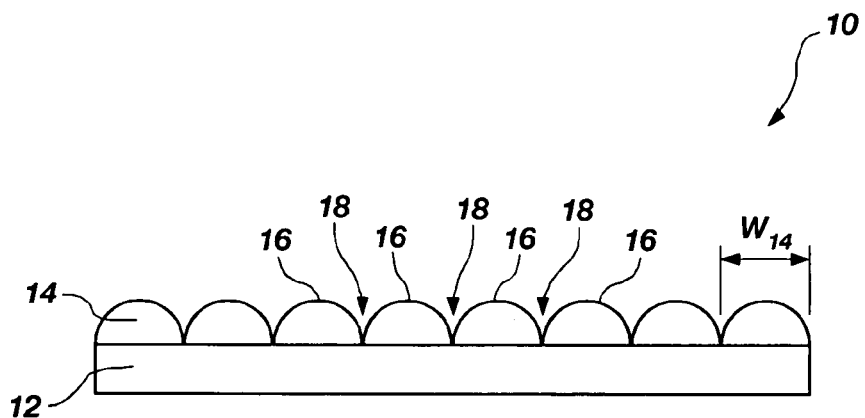
FIG. 3 is an end view of the Raman signal-enhancing structure shown in FIG. 2.

As illustrated in FIG. 3, each protrusion 14 may have a cross-sectional area having a substantially semi-circular shape. Each protrusion 14 may have cross-sectional dimensions of less than about 50 nanometers. By way of example and not limitation, each protrusion 14 may have a width $W_{14}$ of approximately 1-50 nanometers.

The Raman signal-enhancing structure 10 may further include a plurality of edges 18. Each edge 18 may include an intersection between a surface 16 of one protrusion 14 and a surface 16 of an adjacent protrusion 14. By way of example and not limitation, the Raman signal-enhancing structure 10 may include a plurality of linear edges 18, which extend in the Y direction in FIG. 2. The edges 18 may be located on a surface of the substrate 24.

Each protrusion 14 may include a Raman-signal enhancing material such as, for example, gold, platinum, or silver. The substrate 24 may include a substantially planar layer of metal, ceramic, or a polymer material.

The Raman signal-enhancing structure 10 may be used to perform Raman spectroscopy on an analyte, and may be used to enhance the Raman signal emitted by the analyte. The strength of the Raman signal emitted by an analyte may be proportional to the electric field at the location of the analyte.

Figure 1:
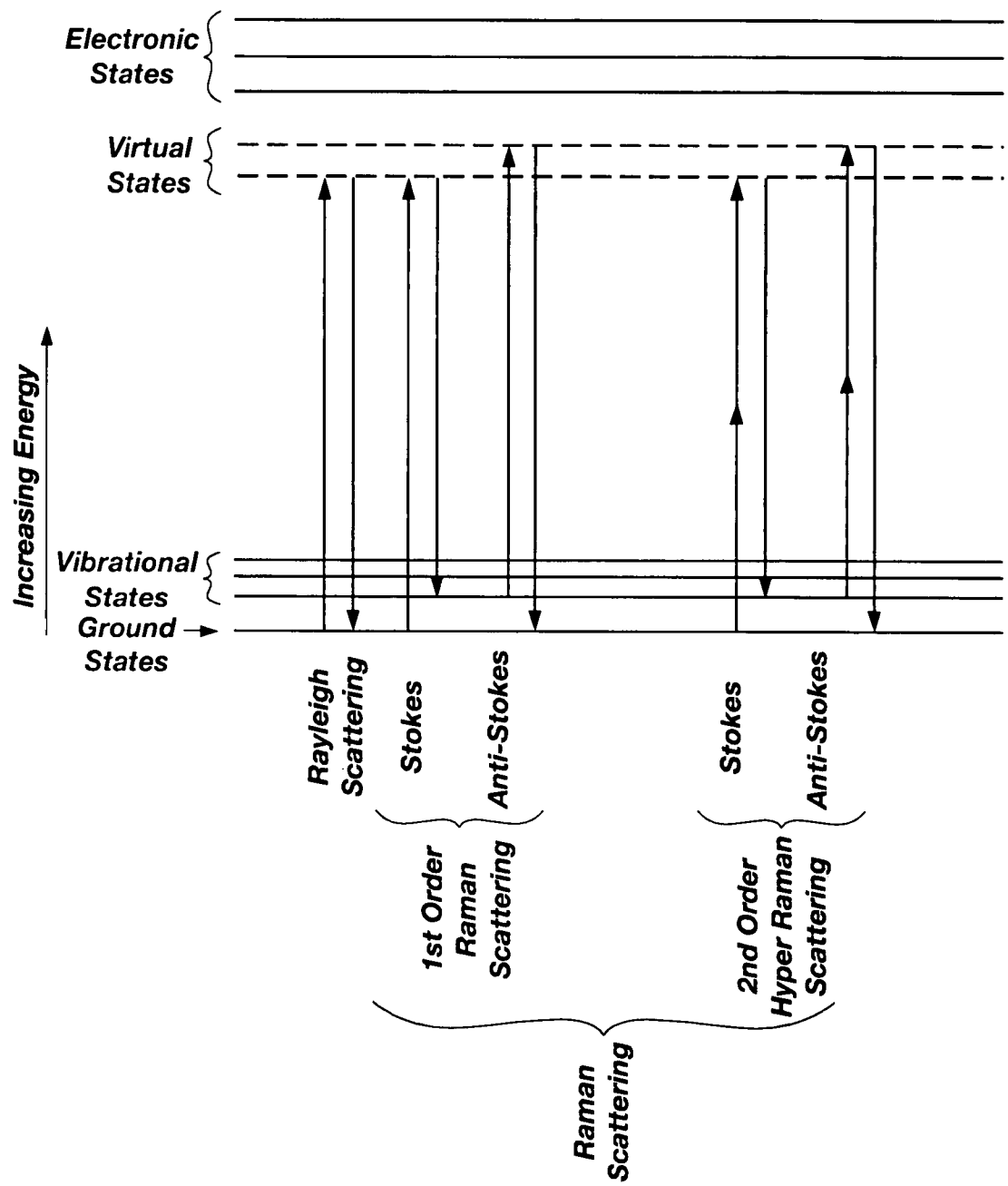
FIG. 1 is a Jablonski energy level diagram schematically representing Rayleigh and Raman scattering processes for a hypothetical analyte.
Figure 4:
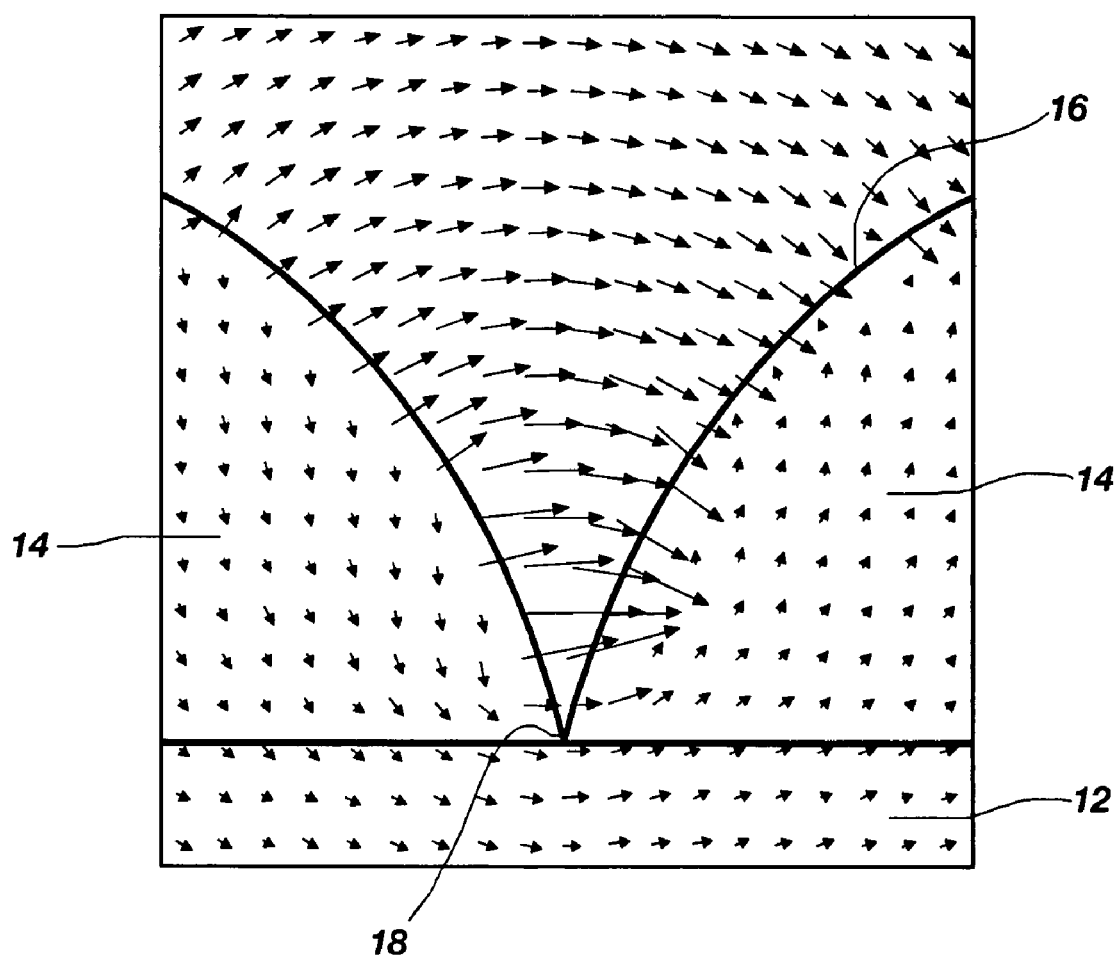
FIG. 4 is an enlarged partial view of the Raman signal-enhancing structure shown in FIGS. 1-2 illustrating an induced electrical field.

FIG. 4 is an enlarged partial view of the Raman signal-enhancing structure 10 shown in FIGS. 1-2 illustrating an electrical field, which may be induced in a region proximate an edge 18 of the Raman signal-enhancing structure 10. As seen in FIG. 4, a very strong local electrical field may be provided in the region proximate the edges 18 of the Raman signal-enhancing structure 10 when the Raman signal-enhancing structure is irradiated with incident electromagnetic radiation. The strength of the Raman signal emitted by an analyte located at or proximate to an edge 18 may be significantly enhanced. Furthermore, an analyte may be attracted to and immobilized at the edges 18 of the Raman signal-enhancing structure 10. As a result, the Raman signal-enhancing structure 10 may significantly enhance the strength of the Raman signal emitted by an analyte when the analyte is provided proximate the Raman signal-enhancing structure 10 and the Raman signal-enhancing structure 10 and the analyte are irradiated with incident electromagnetic radiation.

Figure 5:
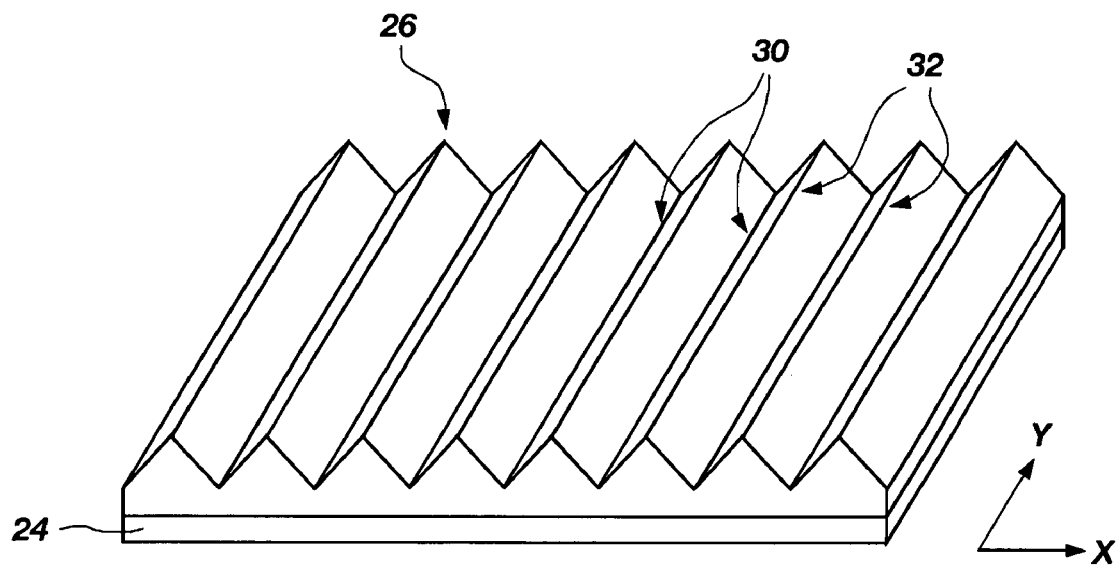
FIG. 5 is a perspective view of another representative Raman signal-enhancing structure that embodies teachings of the present invention.

Another representative Raman signal-enhancing structure 22 that embodies teachings of the present invention is shown in FIG. 5. The Raman signal-enhancing structure 22 may include a substrate 24 and a plurality of protrusions 26 located at predetermined positions on or relative to a surface of the substrate 24. The protrusions 26 may be integrally formed with one another, and the protrusions 26 may be integrally formed with or on the substrate 24. Furthermore, the protrusions 26 may be substantially elongated.

Figure 6:
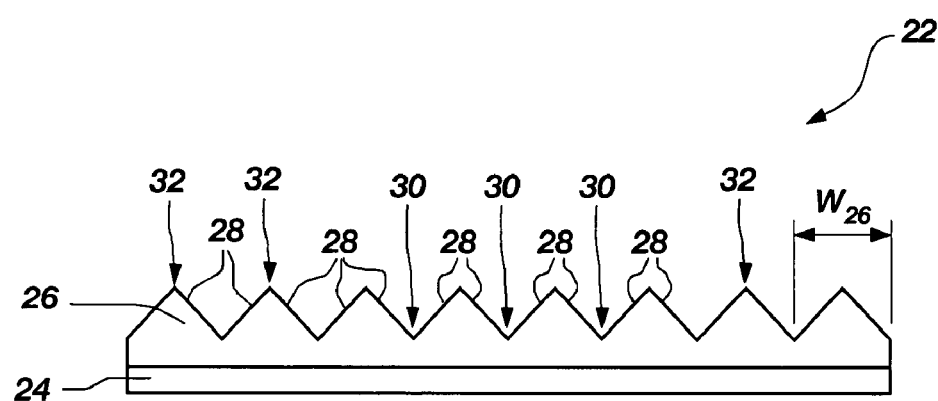
FIG. 6 is an end view of the Raman signal-enhancing structure shown in FIG. 5.

As illustrated in FIG. 6, each protrusion 26 may have a cross-sectional area having a substantially triangular shape. Each protrusion 26 may have cross-sectional dimensions of less than about 50 nanometers. By way of example and not limitation, each protrusion 26 may have a width $W_{26}$ of approximately 1-50 nanometers.

The Raman signal-enhancing structure 22 may further include a first plurality of edges 30 and a second plurality of edges 32. Each edge 30 may include an intersection between a substantially planar surface 28 of one protrusion 26 and a substantially planar surface 28 of an adjacent protrusion 26, and each edge 32 may include an intersection between two substantially planar surfaces 28 of one protrusion 26.

Each protrusion 26 may include a Raman-signal enhancing material such as, for example, gold, platinum, or silver. The substrate 24 may include a substantially planar layer of metal, ceramic, or a polymer material.

The Raman signal-enhancing structure 22, may be used to perform Raman spectroscopy on an analyte in a manner substantially similar to that previously described in relation to the Raman signal-enhancing structure 10 shown in FIGS. 1-3.

Figure 7:
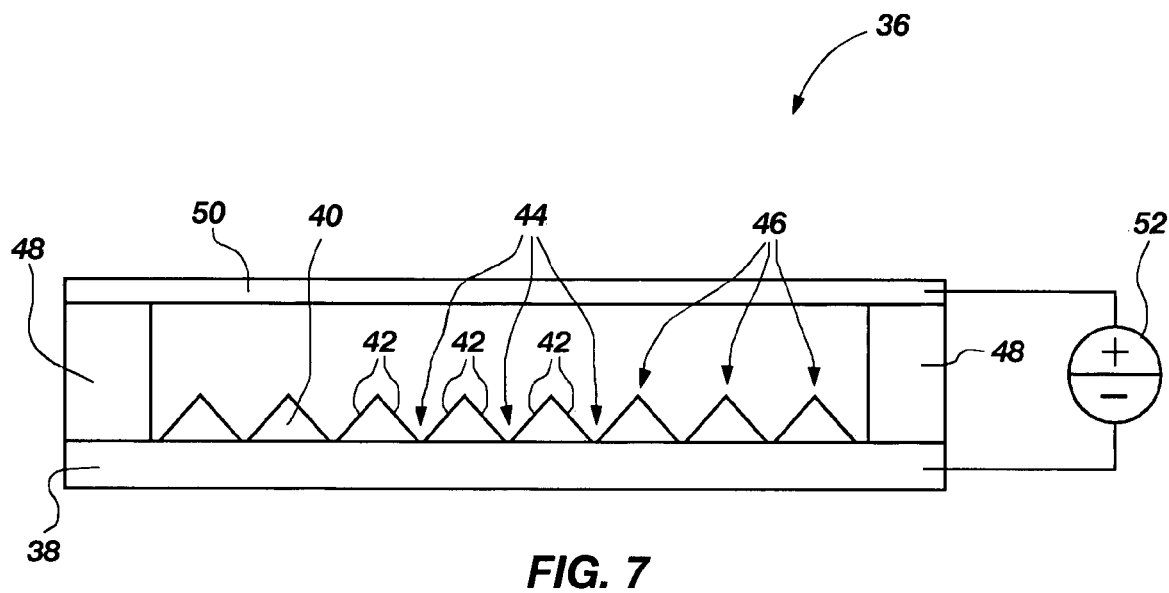
FIG. 7 is an end view of another representative Raman signal-enhancing structure that embodies teachings of the present invention.

Another representative Raman signal-enhancing structure 36 that embodies teachings of the present invention is shown in FIG. 7. The Raman signal-enhancing structure 36 may include a substrate 38 and a plurality of protrusions 40, which may be located at predetermined positions on or relative to a surface of the substrate 38. The protrusions 40 may be integrally formed with or on the substrate 38, and may be substantially elongated. Furthermore, each protrusion 40 may include a nanoparticle and may have a cross-sectional area having a substantially triangular shape. For example, each protrusion 40 may have cross-sectional dimensions of less than about 50 nanometers. Alternatively, the protrusions 40 could include nanoparticles formed separately from the substrate 38 and merely provided on the surface of the substrate 38.

The Raman signal-enhancing structure 36 may include a first plurality of edges 44 and a second plurality of edges 46. Each edge 44 may include an intersection between a substantially planar surface 42 of one protrusion 40 and a substantially planar surface 42 of an adjacent protrusion 40, and each edge 46 may include an intersection between two substantially planar surfaces 42 of one protrusion 40.

Each protrusion 40 may include a Raman-signal enhancing material, and the substrate 24 may include a substantially planar layer of metal, ceramic, or a polymer material.

The Raman signal-enhancing structure 36 may further include at least one electrode 50 positioned proximate the plurality of protrusions 40 and configured to generate an electrical field proximate to or in a region that includes the plurality of protrusions 40. By way of example and not limitation, the electrode 50 may be substantially planar and may include a conductive metal such as, for example, copper. The substantially planar electrode 50 may be oriented substantially parallel to the substrate 38. At least one electrically insulating support structure 48 may be used to support and position the electrode 50 relative to the substrate 38 and the plurality of protrusions 40. By way of example and not limitation, the Raman signal-enhancing structure 36 may include two electrically insulating support structures 48 positioned between the electrode 50 and the substrate 38, as shown in FIG. 7. Each electrically insulating support structure 48 may be attached to each of the electrode 50 and the substrate 38. The substrate 38 may be electrically conductive. Alternatively, the electrode 50 could be separate from the substrate 38 and merely positioned proximate the substrate 38 to allow the electrode 50 to be moved for manipulating the electrical field.

In the embodiment of the invention shown in FIG. 7, the shortest distance between the electrode 50 and any point on a surface 42 of the plurality of protrusions 40 extends between a point on any one of the edges 46 and the electrode 50.

An electrical power source 52 may be provided and configured to apply a voltage between the electrode 50 and the substrate 38, thereby generating an electrical field proximate the plurality of protrusions 40. The electrical field may be used to position an analyte at a selected position on the surface of the Raman signal-enhancing structure 36. Furthermore, if the protrusions 40 include nanoparticles formed separately from the substrate 38 and merely provided on the surface of the substrate 38, the electrical field generated between the electrode 50 and the substrate 38 may be manipulated and used to position and align the nanoparticles on the surface of the substrate 38.

The Raman signal-enhancing structure 36 may be used to perform Raman spectroscopy on an analyte in a manner substantially similar to that previously described in relation to the Raman signal-enhancing structure 10 shown in FIGS. 1-3. An analyte may be provided on a surface of at least one of the protrusions 40 of the Raman signal-enhancing structure 36. If the analyte includes electrically charged particles or regions (such as ions), the analyte may be moved on the surface of the at least one of the protrusions 40 to a location proximate at least one edge 44 or at least one edge 46 of the Raman signal-enhancing structure 36 by applying a voltage between the electrode 50 and the substrate 38 using the power source 52. The analyte and the Raman signal-enhancing structure may be irradiated with electromagnetic radiation, and Raman scattered radiation that is scattered by the analyte may be detected. The electrical field proximate the protrusions 40 induced by incident electromagnetic radiation may be stronger proximate the edges 44 and the edges 46 relative to other locations on the surfaces of the protrusions 40, which may enhance the Raman signal emitted by the analyte.

While not shown in each of the figures, an electrode 50 may be used with any Raman-signal enhancing structure that embodies teachings of the present invention in the same manner as that described in relation to the Raman-signal enhancing structure 36 shown in FIG. 7.

Figure 8:
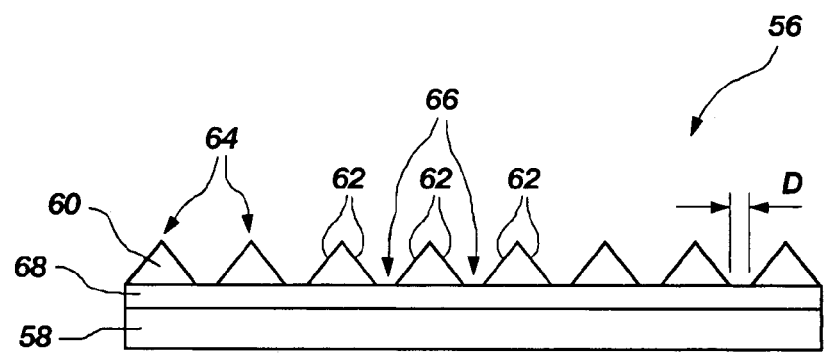
FIG. 8 is an end view of another representative Raman signal-enhancing structure that embodies teachings of the present invention.

Another representative Raman signal-enhancing structure 56 that embodies teachings of the present invention is shown in FIG. 8. The Raman signal-enhancing structure 56 may include a substrate 58 and a plurality of protrusions 60 disposed at selected locations on or relative to a surface of the substrate 58. The protrusions 60 may be substantially identical to the protrusions 40 previously described in relation to the Raman signal-enhancing structure 36 shown in FIG. 7.

The Raman signal-enhancing structure 56 may include a plurality of edges 64. Each edge 64 may include an intersection between two substantially planar surfaces 62 of one protrusion 60. Each protrusion 60 may be separated from adjacent protrusions 60 by a distance D. By way of example and not limitation, the distance D may be less than about five nanometers. A region 66 is located between each pair of adjacent protrusions 60 that includes the shortest distance between the adjacent protrusions 60. In the embodiment shown in FIG. 8, the regions 66 are located near the bases of the protrusions 60 proximate the substrate 58.

Each protrusion 60 may include a Raman-signal enhancing material, and the substrate 58 may include a substantially planar layer of metal, ceramic, or a polymer material.

The Raman signal-enhancing structure 56 may further include a binding material 68 that is configured to bind a selected analyte to the Raman signal-enhancing structure 56 at a location where a strong localized electrical field may be induced. In the embodiment shown in FIG. 8, a strong localized electrical field may be induced in the regions 66, and at least a portion of the binding material 68 may be disposed proximate the regions 66. By way of example and not limitation, a layer of binding material 68 may be disposed on a surface of the substrate 58. The plurality of protrusions 60 may be disposed on the layer of binding material 68, as shown in FIG. 8. In this configuration, the binding material 68 is disposed proximate the regions 66.

Figure 9:
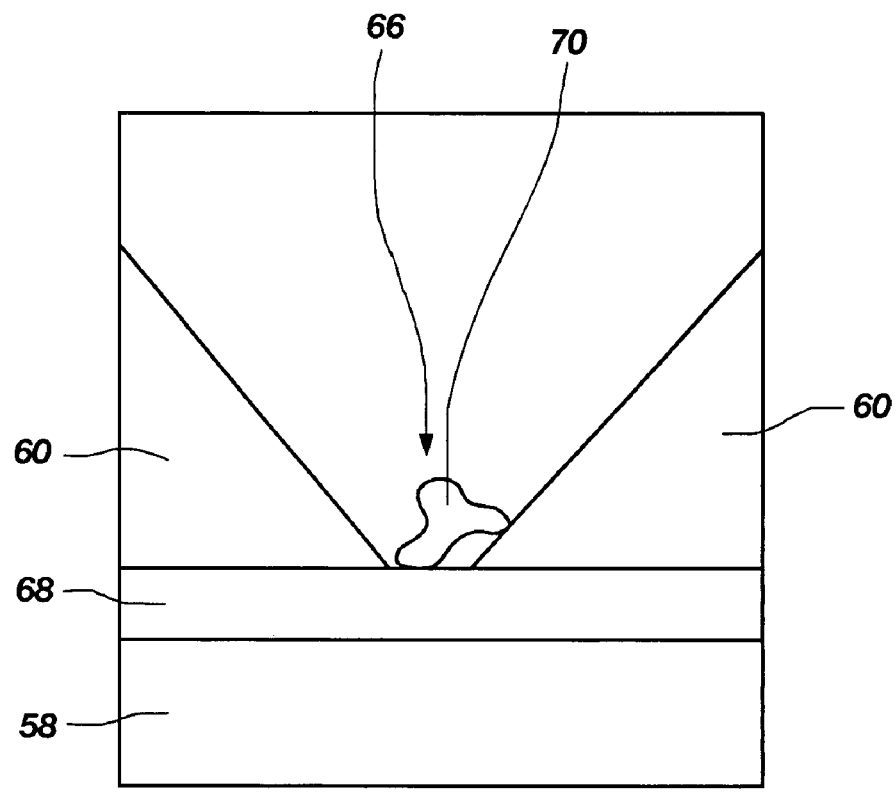
FIG. 9 is an enlarged partial view of the Raman signal-enhancing structure shown in FIG. 8.

FIG. 9 is an enlarged partial view of the Raman signal-enhancing structure 56 shown in FIG. 8. An analyte 70 is shown therein held or bound to the binding material 68 proximate a region 66 between adjacent protrusions 60.

The binding material 68 may include any material to which a selected analyte will preferably bind relative to the protrusions 60. Alternatively, the binding material 68 may include molecules that, together with the selected analyte, form what is known in the art as a "specific pair" or a "recognition pair" of molecules. For example, if the selected analyte is an antigen or an antibody, the binding material 68 may include a complementary antigen or antibody. Many biomolecules act as receptors or ligands to other biomolecules. If the selected analyte is or includes such a biomolecule, the binding material 68 may include a complementary biomolecule.

The Raman signal-enhancing structure 56 may be used to perform Raman spectroscopy on an analyte in a manner substantially similar to that previously described. An analyte 70 having a propensity to bind to the binding material 68 may be provided on a surface of the Raman signal-enhancing structure 56. The analyte 70 may be attracted to the binding material 68, and the binding material 68 may hold or bind the analyte 70 in or proximate to the regions 66. The analyte 70 and the Raman signal-enhancing structure 56 (shown in FIG. 8) may be irradiated with electromagnetic radiation, and Raman scattered radiation that is scattered by the analyte 70 may be detected. As the binding material 68 may hold the analyte 70 in the region or regions 66 in which the induced electrical field may be relatively strong, the Raman signal emitted by the analyte 70 may be enhanced.

Figure 10:
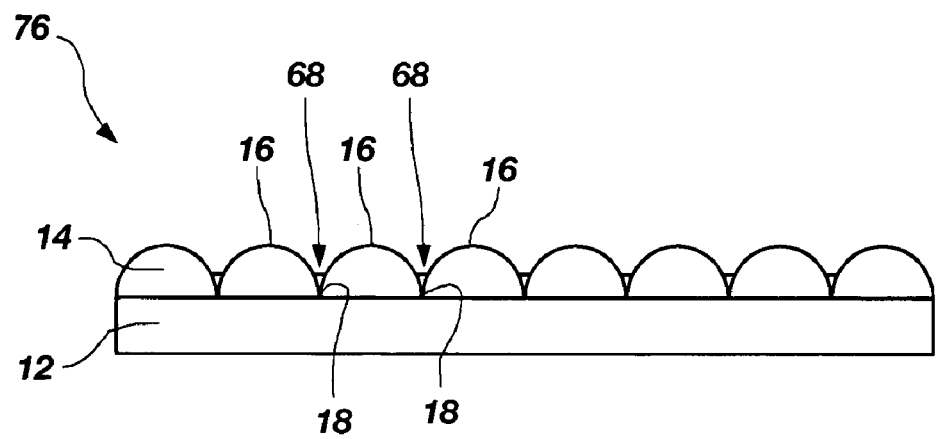
FIG. 10 is an end view of another representative Raman signal-enhancing structure that embodies teachings of the present invention.

Another representative Raman signal-enhancing structure 76 that embodies teachings of the present invention is shown in FIG. 10. The Raman signal-enhancing structure 76 may be substantially similar to the previously described Raman signal-enhancing structure 10 shown in FIGS. 1-4, and includes a substrate 12, a plurality of protrusions 14, and a plurality of edges 18. Each edge 18 may include an intersection between a surface 16 of one protrusion 14 and a surface 16 of an adjacent protrusion 14.

The Raman signal-enhancing structure 76 may further include a binding material 68 that is configured to bind a selected analyte to the Raman signal-enhancing structure 76 at a location where a strong localized electrical field may be induced. In the embodiment shown in FIG. 10, a strong localized electrical field may be induced in the regions proximate the edges 18, and at least a portion of the binding material 90 may be disposed proximate the edges 18.

Figure 11:
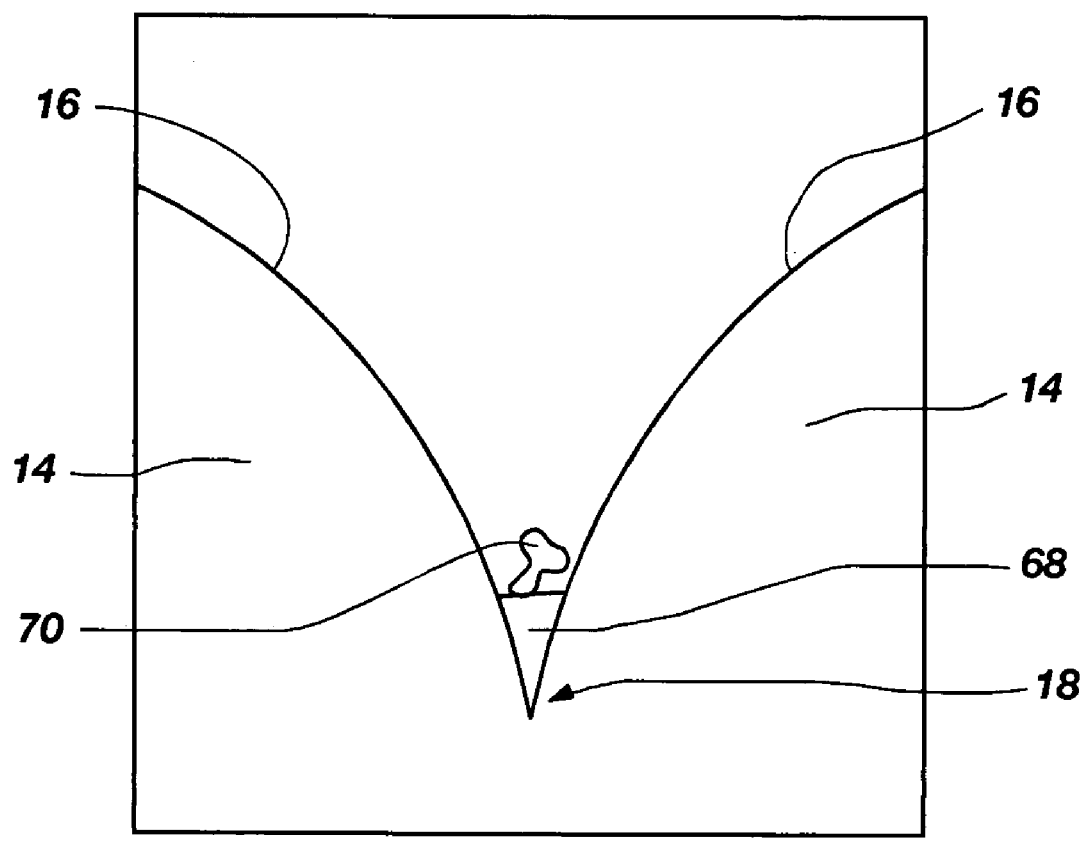
FIG. 11 is an enlarged partial view of the Raman signal-enhancing structure shown in FIG. 10.

By way of example and not limitation, a strip of binding material 68 may be disposed between adjacent protrusions 14 along the edges 18, as shown in FIG. 11. An analyte 70 is shown therein held or bound to the binding material 90 proximate the edge 18 between adjacent protrusions 14.

The Raman signal-enhancing structure 76 (shown in FIG. 10) may be used to perform Raman spectroscopy on an analyte in a manner substantially similar to that previously described. An analyte 70 (FIG. 11) having a propensity to bind to the binding material 68 may be provided on a surface of the Raman signal-enhancing structure 76. The analyte 70 may be attracted to the binding material 90, and the binding material 90 may hold or bind the analyte 70 in or proximate to the edges 18 between adjacent protrusions 14. The analyte 70 and the Raman signal-enhancing structure 76 may be irradiated with electromagnetic radiation, and Raman scattered radiation that is scattered by the analyte 70 may be detected. As the binding material 90 may hold the analyte 70 in the region or regions in which the induced electrical field may be relatively strong, the Raman signal emitted by the analyte 70 may be enhanced.

Raman signal-enhancing structures that embody teachings of the present invention may be formed using techniques known in the art of microdevice and nanodevice fabrication. Such techniques include, for example, lithographic techniques for formation and removal of layers of material or portions of layers of material. One exemplary method that may be used to form Raman signal-enhancing structures that embody teachings of the present invention includes nanoimprint lithography ("NIL"), which is described below with reference to FIGS. 12A-12I.

Figure 12A:
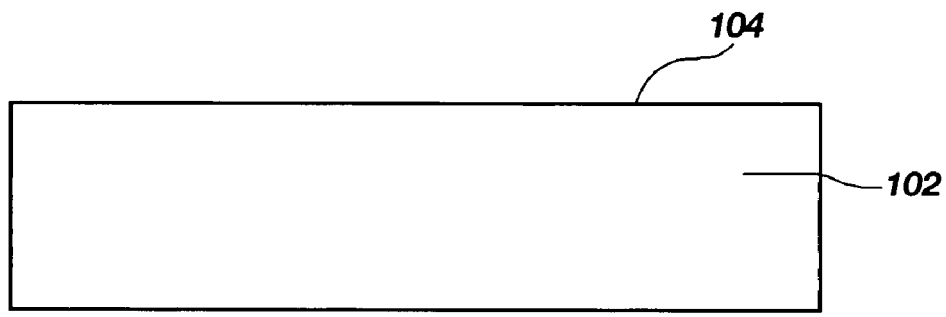
FIGS. 12A-12I illustrate an exemplary method of manufacturing Raman signal enhancing structures that embody teachings of the present invention.
Figure 12B:
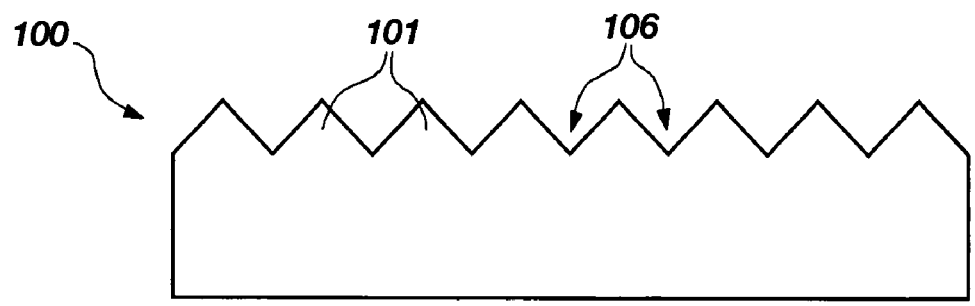

Referring to FIGS. 12A and 12B, a nanoimprint mold 100 (FIG. 12B) may be provided by providing a mold base 102 (FIG. 12A) and forming a plurality of protrusions 101 in a surface 104 of the mold base 102. By way of example and not limitation, the mold base 102 may comprise silica, silicon, quartz, gallium arsenide, or any other suitable metal, ceramic, or polymer material. Furthermore, the protrusions 101 may be formed in the surface 104 of the mold base 102 by, for example, using electron beam lithography, reactive ion etching, and other wet or dry chemical etching methods known in the art to form a plurality of depressions or grooves 106 in the surface 104 of the mold base 102.

Figure 12C:
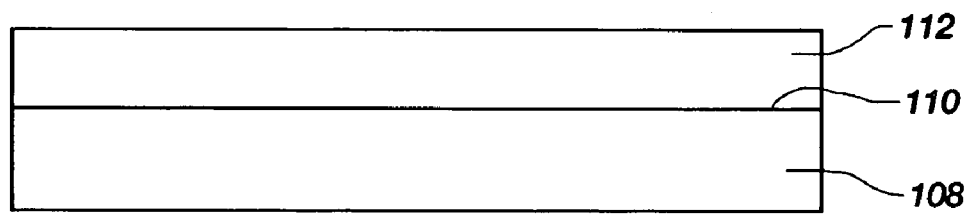

Referring to FIG. 12C, a substrate 108 may be provided and a layer of deformable material 112 may be applied to a surface 110 of the substrate. The layer of deformable material 112 may include, for example, a layer of polymethylmethacrylate (PMMA) or any other commercially available nanoimprint resist. Furthermore, the layer of deformable material 112 may solidify upon application of energy (such as radiation or heat) to the layer of deformable material 112. Such nanoimprint lithography resists are sold by, for example, Nanonex of Monmouth Junction, N.J.

Figure 12D:
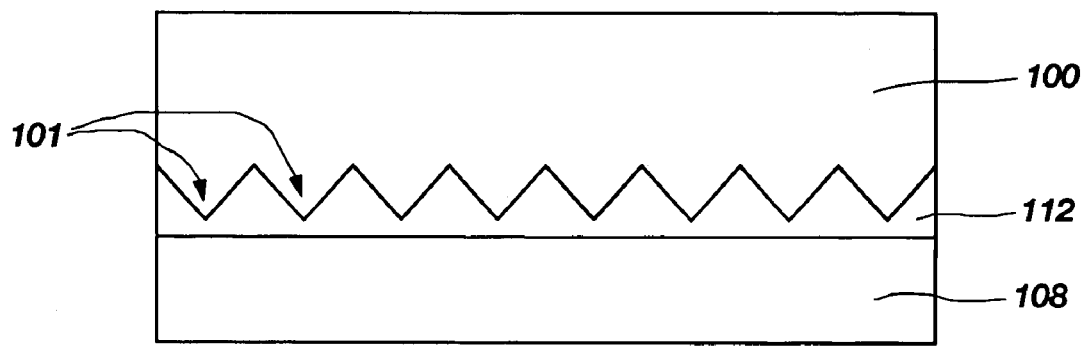
Figure 12E:
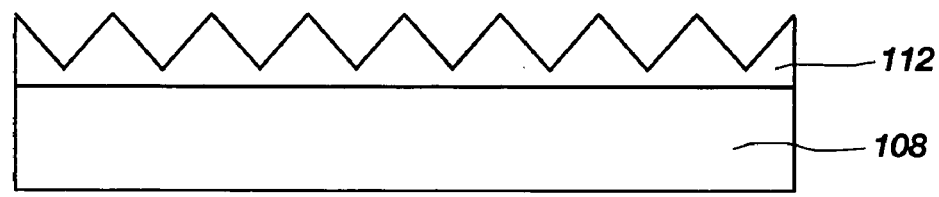

Referring to FIG. 12D, the protrusions 101 of the nanoimprint mold 100 may be pressed into the layer of deformable material 112 to form corresponding protrusions and grooves in the layer of deformable material 112. The layer of deformable material 112 may be cured to solidify the layer of deformable material 112, and the nanoimprint mold 100 may be separated from the substrate 108 and the cured layer of deformable material 112, as shown in FIG. 12E.

Figure 12F:
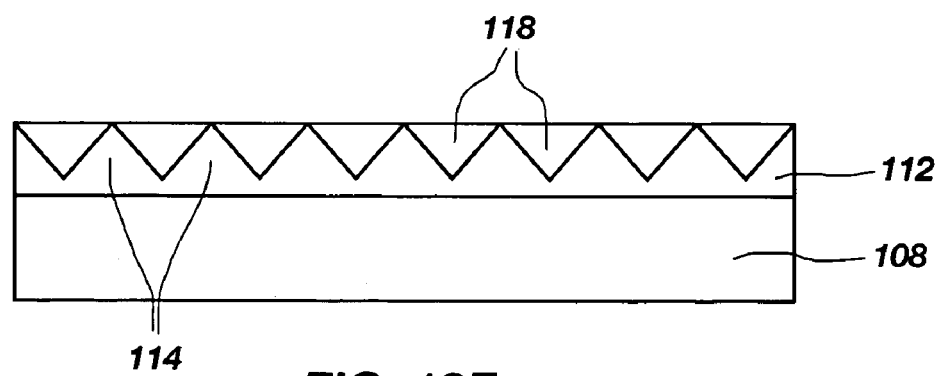

Referring to FIG. 12F, a Raman signal-enhancing material 118 may then be provided in the grooves between protrusions 114 that have been formed in the layer of deformable material 112 using the nanoimprint mold 100. A layer of material 120 may be applied over the Raman signal-enhancing material 118, as shown in FIG. 12G.

Figure 12G:
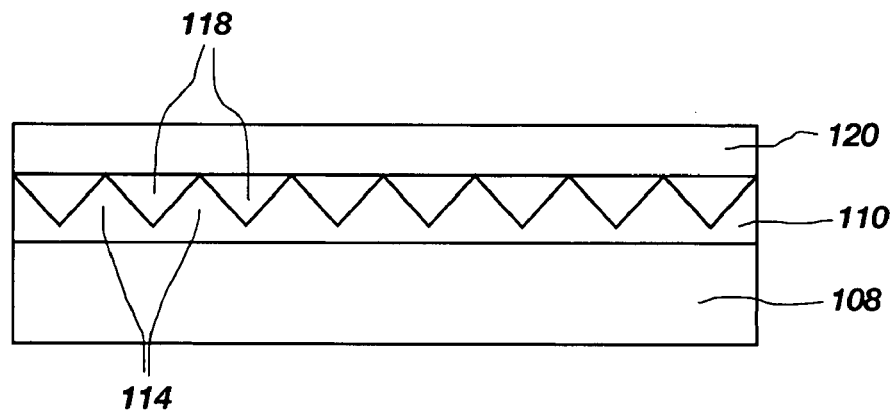

The assembly shown in FIG. 12G can then be inverted, and the substrate 108 and the layer of deformable material 112 may be removed by immersing the assembly in a chemical that will etch or dissolve the layer of deformable material 112 such as, for example, acetone. Alternatively, other removal procedures known in the art may be used, such as, for example, polishing, chemical-mechanical polishing, dry etching, and ion milling.

Figure 12H:
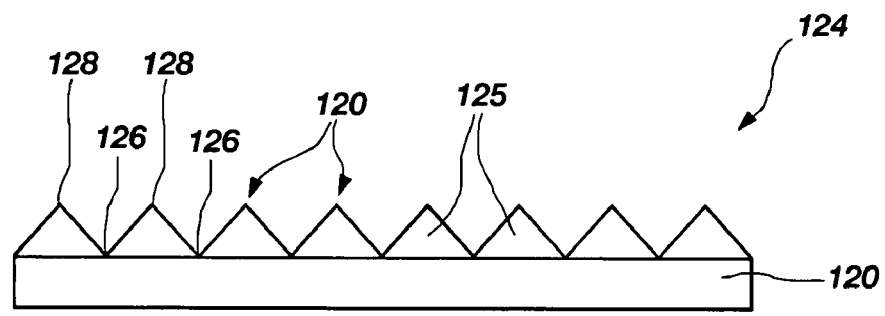

After the substrate 108 and the layer of deformable material 112 have been removed, the layer of material 120 and the Raman signal-enhancing material 118 form a Raman signal-enhancing structure 124 that embodies teachings of the present invention, as shown in FIG. 12H. The Raman signal-enhancing structure 124 includes a plurality of protrusions 125, which comprise the Raman signal-enhancing material 118 (FIG. 12G). The layer of material 120 provides a substrate of the Raman signal-enhancing structure 124. Furthermore, the Raman signal-enhancing structure 124 may include a first plurality of edges 126 and a second plurality of edges 128. Each edge 126 may include an intersection between a substantially planar surface of one protrusion 125 and a substantially planar surface of an adjacent protrusion 125, and each edge 128 may include an intersection between two substantially planar surfaces of one protrusion 125.

Figure 12I:
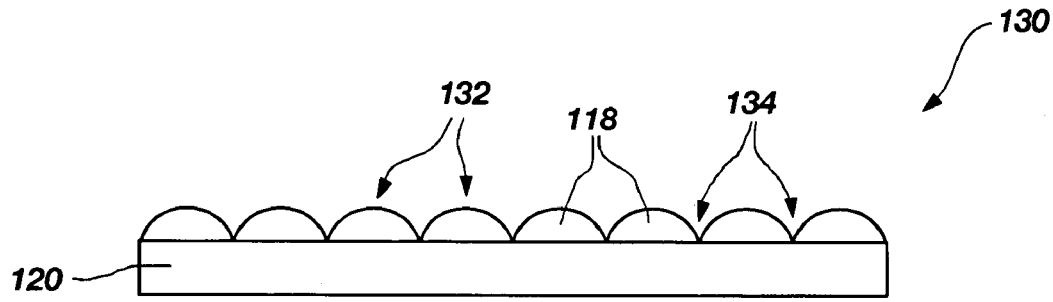

The Raman signal-enhancing structure 124 shown in FIG. 12H may be further processed by, for example, annealing the Raman signal-enhancing structure 124 at a temperature just below the melting point of the Raman signal-enhancing material 118 of the protrusions 125 to provide the Raman signal-enhancing structure 130 shown in FIG. 12I, which also embodies teachings of the present invention. The Raman signal-enhancing structure 130 is substantially similar to the previously described Raman signal-enhancing structure 10 shown in FIG. 2, and includes a plurality of protrusions 132 located at predetermined positions on or relative to a surface of a substrate 120. The Raman signal-enhancing structure 130 also may include a plurality of edges 134.

Raman signal-enhancing structures that embody teachings of the present invention may be used in Raman spectroscopy systems to perform Raman spectroscopy on an analyte.

Figure 13:
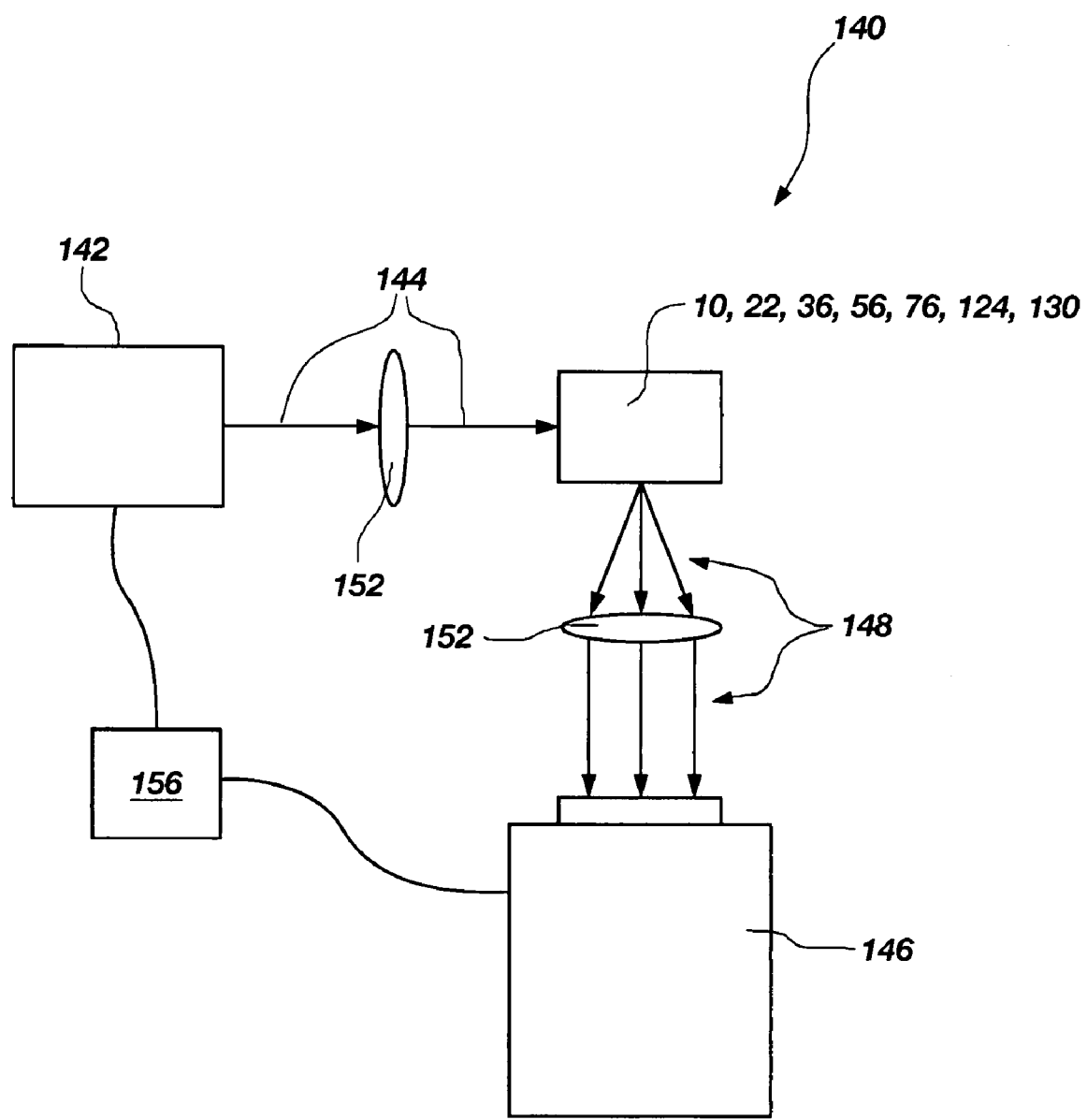
FIG. 13 is a schematic diagram of a Raman spectroscopy system that embodies teachings of the present invention.

FIG. 13 is a schematic diagram of an exemplary Raman spectroscopy system 140 that embodies teachings of the present invention. The Raman spectroscopy system 140 includes an electromagnetic radiation source 142 that is configured to provide incident radiation 144, an electromagnetic radiation detector 146 that is configured to detect Raman scattered radiation 148 that is scattered by an analyte, and a Raman signal-enhancing structure that embodies teachings of the present invention, such as, for example, any one of the previously described Raman signal-enhancing structures 10, 22, 36, 56, 76, 124, and 130. The Raman spectroscopy system 140 also may include various optical components 152 (such as, for example, apertures, lenses, and filters) positioned between the electromagnetic radiation source 142 and the Raman signal-enhancing structure 10, 22, 36, 56, 76, 124, 130, and between the Raman signal-enhancing structure and the radiation detector 146.

The radiation source 142 may include any suitable source for emitting incident electromagnetic radiation 144 at a desired wavelength and may be capable of emitting a tunable wavelength of monochromatic incident electromagnetic radiation 144. For example, commercially available semiconductor lasers, helium-neon lasers, carbon dioxide lasers, radiation emitting diodes, incandescent lamps, vertical cavity surface emitting lasers, edge emitting lasers, and many other known radiation emitting sources can be used as the electromagnetic radiation source 142. If necessary, a radiation filter may be used in conjunction with the electromagnetic radiation source 142 to provide monochromatic incident electromagnetic radiation 144. The wavelengths that are emitted by the electromagnetic radiation source 142 may be any suitable wavelength for performing Raman spectroscopy on the analyte, and may be within or near the visible region of the electromagnetic radiation spectrum.

The radiation detector 146 receives and detects the Raman scattered radiation 148 that includes Raman scattered photons that are scattered by an analyte located proximate the Raman signal-enhancing structure 10, 22, 36, 56, 76, 124, 130. The radiation detector 146 may include a device for determining the wavelength of the Raman scattered radiation 148 and a device for determining the intensity of the Raman scattered radiation 148. By way of example and not limitation, the radiation detector 146 may include a monochromator and a photomultiplier tube. As another example, the radiation detector 146 may include a wavelength dispersive grating and a charge coupled device. Typically, the Raman scattered radiation 148 is scattered in all directions relative to the Raman signal-enhancing structure.

Optical components 152 positioned between the electromagnetic radiation source 142 and the Raman signal-enhancing structure 10, 22, 36, 56, 76, 124, 130 can be used to collimate, filter, or focus the incident electromagnetic radiation 144 before the incident electromagnetic radiation 144 impinges on the Raman signal-enhancing structure and the analyte. Optical components 152 positioned between the Raman signal-enhancing structure 10, 22, 36, 56, 76, 124, 130 and the radiation detector 146 can be used to collimate, filter, or focus the Raman scattered radiation 148.

Raman spectroscopy system 140 also may include a system controller 156 for controlling the radiation source 142, the radiation detector 146, and any controllable components of the Raman signal-enhancing structure 10, 22, 36, 56, 76, 124, 130 (such as, for example, the power source 52 shown in FIG. 7). The system controller may include an input system for allowing a user to control the operation of the components of the Raman spectroscopy system 140, and an output system for displaying or otherwise conveying information obtained from the Raman scattered radiation 148. The system controller may also a computer devise including a signal processor and memory for collecting, storing, and otherwise manipulating data relating to the Raman signal obtained from the radiation detector 146.

It should be understood that Raman spectroscopy systems that embody teachings of the present invention may be provided in many forms, such as, for example, conventional table top systems or small portable Raman spectroscopy systems. For example, an exemplary Raman spectroscopy system that embodies teachings of the present invention may include a probe comprising one of the previously described Raman signal-enhancing structures 10, 22, 36, 56, 76, 124, 130. Fiber optic cables or wires may be used to transport the incident electromagnetic radiation 144 from the radiation source 144 to the probe and to deliver Raman scattered radiation 148 from the probe to the radiation detector 146. The radiation source 142 and the radiation detector 146 may be provided in a single portable unit to provide a relatively small, portable Raman spectroscopy system.

The structures, systems, and methods described herein may be used to improve the sensitivity of currently available Raman spectroscopy systems and to improve known techniques for performing Raman spectroscopy. Furthermore, at least one of the intensity, uniformity, and homogeneity of a Raman signal emitted by an analyte may be enhanced using the structures, systems, and methods described herein. Furthermore, the Raman signal-enhancing structures and Raman spectroscopy systems described herein may be used to perform hyper-Raman spectroscopy and to enhance the hyper-Raman scattered radiation.

The performance of molecular sensors, nanoscale electronics, optoelectronics, and other devices employing the Raman Effect may be improved by using Raman signal-enhancing structures, Raman spectroscopy systems, and methods that embody teachings of the present invention.

Although the foregoing description contains many specifics, these are not to be construed as limiting the scope of the present invention, but merely as providing certain representative embodiments. Similarly, other embodiments of the invention can be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A Raman signal-enhancing structure comprising:
   a substrate;
   a plurality of protrusions located at predetermined positions relative to a surface of the substrate, each protrusion of the plurality of protrusions comprising a Raman signal-enhancing material and having cross-sectional dimensions of less than about 50 nanometers, each protrusion comprising at least one surface; and
   a plurality of edges, each edge comprising an intersection between two nonparallel surfaces of at least one protrusion.

2. The Raman signal-enhancing structure of claim 1, further comprising at least one electrode positioned proximate the plurality of protrusions and configured to generate an electrical field proximate the plurality of protrusions.

3. The Raman signal-enhancing structure of claim 2, wherein the shortest distance between the at least one electrode and any point on a surface of the plurality of protrusions extends between a point on at least one edge of the plurality of edges and the at least one electrode.

4. The Raman signal-enhancing structure of claim 2, further comprising an electrically insulating support structure attached to the substrate and the at least one electrode, the electrically insulating support structure supporting the at least one electrode relative to the substrate.

5. The Raman signal-enhancing structure of claim 2, further comprising a voltage source configured to provide a voltage between the at least one electrode and the substrate.

6. The Raman signal-enhancing structure of claim 1, wherein at least one edge of the plurality of edges comprises an intersection between two nonparallel surfaces of one protrusion of the plurality of protrusions.

7. The Raman signal-enhancing structure of claim 1, wherein at least one edge of the plurality of edges comprises an intersection between a surface of a first protrusion and a surface of a second protrusion.

8. The Raman signal-enhancing structure of claim 1, wherein each protrusion of the plurality of protrusions is substantially elongated.

9. The Raman signal-enhancing structure of claim 8, wherein each protrusion of the plurality of protrusions has a cross-sectional area having a triangular or semi-circular shape.

10. The Raman signal-enhancing structure of claim 9, wherein each protrusion of the plurality of protrusions has a width of from about 1 nanometer to about 50 nanometers.

11. The Raman signal-enhancing structure of claim 1, wherein each protrusion of the plurality of protrusions is attached to the substrate.

12. The Raman signal-enhancing structure of claim 11, wherein each protrusion of the plurality of protrusions is integrally formed with the substrate.

13. The Raman signal-enhancing structure of claim 1, wherein the Raman signal-enhancing material comprises gold, platinum, or silver.

14. The Raman signal-enhancing structure of claim 1, further comprising a binding material configured to bind a selected analyte to the Raman signal-enhancing structure, the binding material being selectively located proximate at least one edge of the plurality of edges.

15. The Raman signal-enhancing structure of claim 14, wherein the binding material comprises a biomolecule, the biomolecule and a selected analyte on which Raman spectroscopy is to be performed using the Raman signal-enhancing structure forming a specific pair.

16. The Raman signal-enhancing structure of claim 1, further comprising a structure configured to position an analyte proximate at least one edge of the plurality of edges.

17. The Raman signal-enhancing structure of claim 16, wherein the structure configured to position an analyte proximate at least one edge comprises an electrode configured to generate an electrical field proximate the Raman signal-enhancing structure or a binding material configured to bind a selected analyte to the Raman signal-enhancing structure.

18. The Raman signal-enhancing structure of claim 1, further comprising:
   a source configured to provide incident electromagnetic radiation; and
   a detector configured to detect Raman scattered radiation.

19. A method of forming a Raman signal-enhancing structure for use in a spectroscopy system, the method comprising:
   providing a nanoimprint mold comprising a plurality of protrusions extending from a surface of the mold;
   providing a substrate;
   applying a layer of deformable material to a surface of the substrate;
   pressing the plurality of protrusions of the nanoimprint mold into the layer of deformable material to form a plurality of complementary protrusions in the layer of deformable material;
   removing the nanoimprint mold from the layer of deformable material;

applying a Raman signal-enhancing material over the complementary protrusions in the layer of deformable material to form a plurality of protrusions comprising a Raman-signal enhancing material; and separating the substrate and the layer of deformable material from the plurality of protrusions comprising a Raman-signal enhancing material.

20. A method of performing Raman spectroscopy on an analyte, the method comprising:

providing a Raman signal-enhancing structure comprising:

at least one edge, the at least one edge comprising an intersection between two nonparallel surfaces of the Raman signal-enhancing structure; and a structure configured to position an analyte proximate the at least one edge;

providing an analyte proximate the Raman signal-enhancing structure;

positioning the analyte proximate the at least one edge using the structure configured to position the analyte;

irradiating the analyte with electromagnetic radiation; and detecting Raman scattered radiation that is scattered by the analyte.

* * * * *